United States Patent
Reynolds et al.

(10) Patent No.: US 7,799,932 B2
(45) Date of Patent: Sep. 21, 2010

(54) N-SUBSTITUTED 3,4-ALKYLENEDIOXYPYRROLES, ESTER SUBSTITUTED DIHYDROXYPYRROLES AND METHODS FOR SYNTHESIS OF THESE PYRROLES

(75) Inventors: John R. Reynolds, Gainesville, FL (US); Ryan M. Walczak, Gainesville, FL (US); John Sigure Cowart, II, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 11/990,042

(22) PCT Filed: Oct. 6, 2006

(86) PCT No.: PCT/US2006/039958

§ 371 (c)(1),
(2), (4) Date: Apr. 8, 2008

(87) PCT Pub. No.: WO2007/041724

PCT Pub. Date: Apr. 12, 2007

(65) Prior Publication Data

US 2009/0149661 A1      Jun. 11, 2009

Related U.S. Application Data

(60) Provisional application No. 60/724,178, filed on Oct. 6, 2005.

(51) Int. Cl.
C07D 207/36 (2006.01)
(52) U.S. Cl. .................. 548/453; 548/533
(58) Field of Classification Search .......... 548/453, 548/533
See application file for complete search history.

(56) References Cited

U.S. PATENT DOCUMENTS 6,734,312 B2    5/2004    Reynolds et al.

FOREIGN PATENT DOCUMENTS

WO    WO 2007/041724 A1    4/2007

OTHER PUBLICATIONS

Dallacker et al. Chemische Berichte (1975), 108 (2), p. 569-575.*
Kim, I. T., et al., "New Conducting Polymers Based on Poly(3,4-ethylenedioxypyrrole): Synthesis, Characterization, and Properties" *Chemistry Letters*, 2004, p. 46, vol. 33, No. 1.

(Continued)

*Primary Examiner*—Kamal A Saeed
*Assistant Examiner*—Valerie Rodriguez-Garcia
(74) *Attorney, Agent, or Firm*—Saliwanchik, Lloyd & Saliwanchik

(57) ABSTRACT

A family of N-substituted 3,4-alkylenedioxypyrrole includes monomers for of formula (I) electropolymerization to conjugated polymers and key intermediates for the preparation of the monomers. The preparation of the //-substituted 3,4-alkylenedioxypyrroles is carried out via a synthetic intermediate, an ester substituted dihydroxypyrrole. The synthetic method to prepare the //-substituted 3,4-alkylenedioxypyrrole intermediates and ultimately the N-substituted 3,4-alkylenedioxypyrrole monomers begins with a reaction to form the ester substituted dihydroxypyrrole.

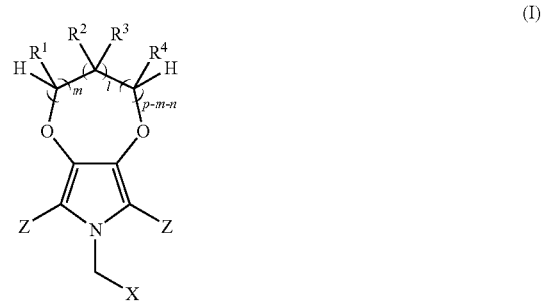

11 Claims, 10 Drawing Sheets

OTHER PUBLICATIONS

Sonmez, G., et al., "N-Substituted Poly(3,4-propylenedioxypyrrole)s: High Gap and Low Redox Potential Switching Electroactive and Electrochromic Polymers," *Macromolecules*, 2003, pp. 639-647, vol. 36.

Zong, K. et al. "3, 4-Alkylenedioxypyrroles: Functionalized Derivatives as Monomers for New Electron-Rich Conducting and Electroactive Polymers," *J. Org. Chem*, 2001, pp. 6873-6882, vol. 66, No. 21.

Walczak, R. M. et al. "Poly (3, 4-Alkylenedioxypyrroles): The PXDOPs as Versatile Yet Underutilized Electroactive and Conducting Polymers," *Adv. Mater.*, 2006, pp. 1121-1131, vol. 18.

Dallacker, F., et al., "Methylenedioxyhetarenes 1. Preparation of 3.4-methylenedioxythiophene, furan, and—pyrrole derivatives", Database CA, Chemical Abstracts Service, Columbus, Ohio, US, 1975.

* cited by examiner

N-SUBSTITUTED 3,4-ALKYLENEDIOXYPYRROLES, ESTER SUBSTITUTED DIHYDROXYPYRROLES AND METHODS FOR SYNTHESIS OF THESE PYRROLES

CROSS-REFERENCE TO RELATED APPLICATIONS

This application is the National Stage of International Application Number PCT/US2006/039958, filed Oct. 6, 2006, which claims the benefit of U.S. Provisional Application No. 60/724,178, filed Oct. 6, 2005, each of which is hereby incorporated by reference herein in its entirety, including any figures, tables, nucleic acid sequences, amino acid sequences, or drawings.

FIELD OF THE INVENTION

The invention is directed to ester substituted dihydroxypyrroles, N-substituted 3,4-alkylenedioxypyrroles, and a method of synthesis of the ester substituted dihydroxypyrroles and N-substituted 3,4-alkylenedioxypyrroles.

BACKGROUND OF THE INVENTION

The family of poly(3,4-alkylenedioxypyrroles) are known to be useful polymers for the fabrication of a wide variety of products. Useful monomers for this family of polymers include N-alkylated 3,4-alkylenedioxypyrroles. Such products include electrochromic windows, mirrors and displays, electronic paper, anti-stat conductors, transparent conductors, field effect transistors, supercapacitors, batteries, photovoltaic devices, and other electronic components due to their elevated band gaps, low oxidation potentials, biological activity, and flexibility toward functionalization. Present synthetic routes to the N-alkylated 3,4-alkylenedioxypyrrole monomers are expensive as the synthetic pathways are difficult and inefficient and their isolation typically requires chromatography which significantly raises the cost and significantly limits the product throughput provided by the process.

To illustrate the present state of the art, a prior art synthetic pathway is described below for the synthesis of a soluble N-alkylated 3,4-alkylenedioxypyrrole, N-(octyl)-3,4-propylenedioxypyrrole, as disclosed by Sönmez, G.; Schwendeman, I.; Schottland, P.; Zong, K.; Reynolds, J. R. *Macromolecules* 2003, 36, 639-647. FIG. 1 illustrates this method for N-(2-ethylhexyl)-3,4-propylenedioxypyrrole. The synthesis begins with the reaction of benzylamine with methyl bromoacetate to yield a diester which undergoes the heterocyclic ring-formation via a Hinsberg condensation with diethyloxylate to yield a dihydroxypyrrole. The propylene bridge is then formed via Williamson etherification of the dihydroxypyrrole with 1,3-dibromopropane to yield an ester substituted 3,4-propylenedioxypyrrole. The next step involves the catalytic debenzylation of the ester substituted 3,4-propylenedioxypyrrole in glacial acetic acid with a palladium catalyst over a period of five days. The resulting diester hydropyrrole, is then saponified to yield a diacid, which is then converted to propylenedioxypyrrole via decarboxylation in triethanolamine. Propylenedioxypyrrole is then functionalized to yield a derivative, such as N-(2-ethylhexyl)propylenedioxypyrrole.

This pathway is undesirable from a commercial standpoint for several reasons. This synthesis of a soluble propylenedioxypyrrole requires seven transformations, two of which require a protected nitrogen using an atom inefficient benzyl group and its subsequent deprotection. In particular, the fourth step that yields an ester substituted 3,4-propylenedioxypyrrole is undesirable from a commercial standpoint due to its long reaction time, expensive reagents, and the use of a toxic palladium catalyst.

There remains a need to develop a method of preparing N-substituted 3,4-alkylenedioxypyrroles in a manner that is efficient and cost effective with less toxic reagents and catalysts. There also is a need for flexible intermediates such that N-substituted 3,4-alkylenedioxypyrroles with a wide variety of substituents can be formed such that the structure of these monomers and ultimately the polymers from them can be modified to develop properties needed for existing and future uses of the conjugated poly(3,4-alkylenedioxypyrrole)s.

BRIEF DESCRIPTION OF THE DRAWINGS

There are shown in the drawings, embodiments which are presently preferred, it being understood, however, that the invention is not limited to the particular molecules and methods illustrated.

SUMMARY OF THE INVENTION

Figure 1:
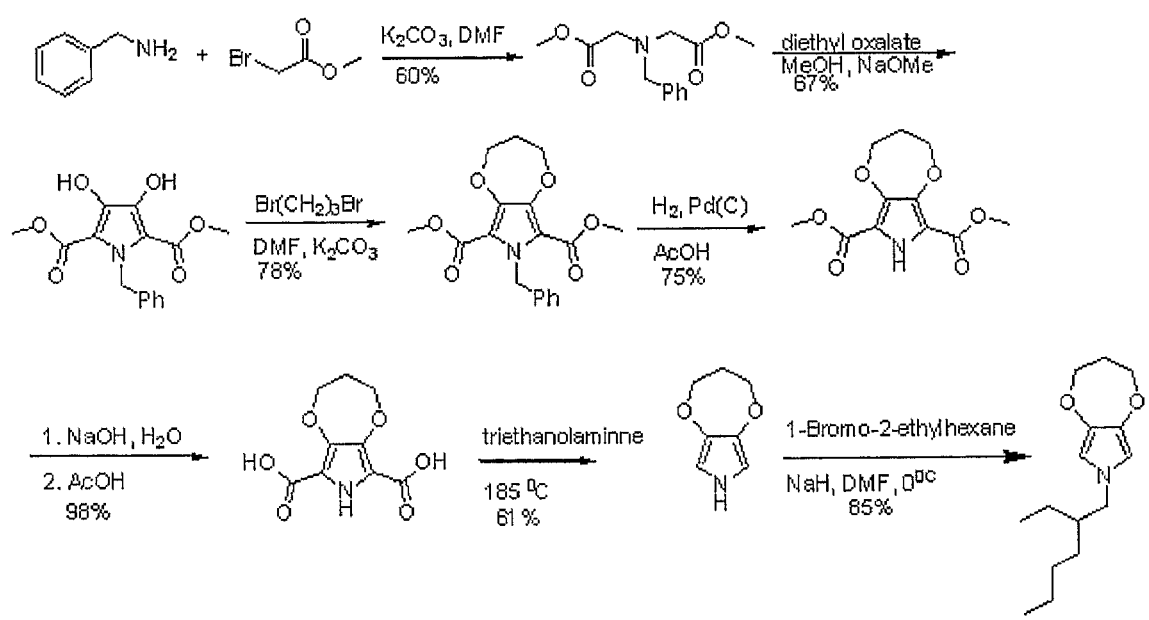
FIG. 1 shows a well practiced prior art synthetic route for obtaining N-alkylated 3,4-alkylenedioxypyrrole derivatives.

A composition of matter for a family of novel N-substituted 3,4-alkylenedioxypyrrole of the structure:

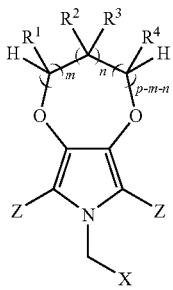

where: $R^1$, $R^2$, $R^3$, and $R^4$ are independently hydrogen, methyl, ethyl, $C_3$ through $C_{20}$ straight or branched chain alkyl, aryl, or alkylaryl; p is 2 through 6, m is 1 through p−1, n is 0 through p−2; Z is H or C(O)OR, wherein R is hydrogen, methyl, ethyl, $C_3$ through $C_{20}$ straight or branched chain alkyl; and X is $C(O)R^5$, $CH_2YR^6$, or $CR^7=CR^8R^9$, where $R^5$ is hydrogen, methyl, ethyl, $C_3$ through $C_{20}$ straight or branched chain alkyl, aryl, $OR^{10}$, or $NR^{11}R^{12}$, where $R^{10}$, $R^{11}$, and $R^{12}$, are independently hydrogen, methyl, ethyl, $C_3$ through $C_{20}$ straight or branched chain alkyl, aryl or alkylaryl, wherein Y is O, OC(O), $NR^{13}$, or $NR^{14}C(O)$, and where $R^6$, $R^7$, $R^8$, $R^9$, $R^{13}$, and $R^{14}$ are independently hydrogen, methyl, ethyl, $C_3$ through $C_8$ straight or branched chain alkyl, aryl, or alkylaryl.

A synthetic intermediate to prepare the family of N-substituted 3,4-alkylenedioxypyrroles is an ester substituted dihydroxypyrrole of the structure:

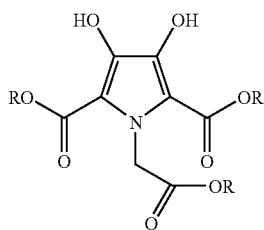

where the three R groups are independently methyl, ethyl, $C_3$ through $C_{20}$ straight or branched chain alkyl, or aryl. The useful ester substituted dihydroxypyrrole can have R being ethyl.

A method for preparing N-substituted 3,4-alkylenedioxypyrroles involves the steps of: providing a nitrogen triester of the structure: $N(CH_2C(O)OR)_3$ where the three R groups are independently methyl, ethyl, $C_3$ through $C_{20}$ straight or branched chain alkyl, or aryl; condensing the nitrogen triester with dimethyl or diethyloxalate to form an ester substituted dihydroxypyrrole of the structure:

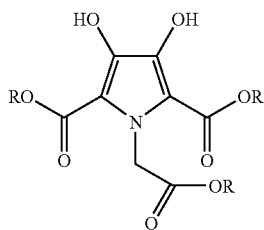

where the three R groups are independently methyl, ethyl, $C_3$ through $C_{20}$ straight or branched chain alkyl, or aryl; annulating the ester substituted dihydroxypyrrole with a difunctionalalkylene of the structure: $W(CHR^1)_m(CR^2R^3)_n(CHR^4)_{p-m-n}W$ where W is Cl, Br, I, sulfate, or sulfonate, $R^1$, $R^2$, $R^3$, and $R^4$ are independently hydrogen, methyl, ethyl, $C_3$ through $C_{20}$ straight or branched chain alkyl, aryl, or alkylaryl; p is 2 through 6, m is 1 through p−1, n is 0 through p−2, to form an ester substituted alkylenedioxypyrrole of the structure:

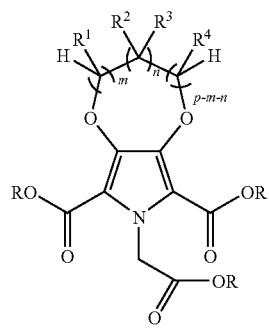

where the three R groups are independently methyl, ethyl, $C_3$ through $C_{20}$ straight or branched chain alkyl, or aryl, $R^1$, $R^2$, $R^3$, and $R^4$ are independently hydrogen, methyl, ethyl, $C_3$ through $C_{20}$ straight or branched chain alkyl, aryl, or alkylaryl, and p is 2 through 6, m is 1 through p−1, n is 0 through p−2; saponifying and neutralizing of the ester substituted alkylenedioxypyrrole to form an acid substituted 3,4-alkylenedioxypyrrole of the structure:

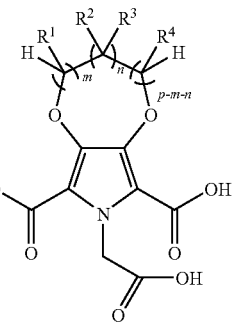

where $R^1$, $R^2$, $R^3$, and $R^4$ are independently hydrogen, methyl, ethyl, $C_3$ through $C_{20}$ straight or branched chain alkyl, aryl, or alkylaryl, and p is 2 through 6, m is 1 through p−1, n is 0 through p−2; decarboxylating of said acid substituted 3,4-alkylenedioxypyrrole to form a 3,4-alkylenedioxypyrrole-acetic acid of the structure:

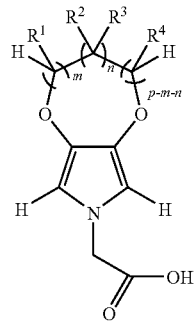

wherein $R^1$, $R^2$, $R^3$, and $R^4$ are independently hydrogen, methyl, ethyl, $C_3$ through $C_{20}$ straight or branched chain alkyl, aryl, or alkylaryl, and p is 2 through 6, m is 1 through p−1, n is 0 through p−2; and transforming of the 3,4-alkylenedioxypyrrole-acetic acid by a single reaction or a series of reactions into the N-substituted 3,4-alkylenedioxypyrrole of the structure:

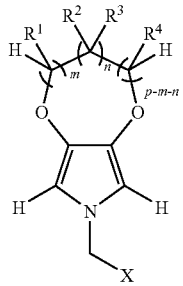

where: $R^1$, $R^2$, $R^3$, and $R^4$ are independently hydrogen, methyl, ethyl, $C_3$ through $C_{20}$ straight or branched chain alkyl, aryl, or alkylaryl; p is 2 through 6, m is 1 through p−1, n is 0 through p−2; and X is $C(O)R^5$, $CH_2YR^6$, or $CR^7{=}CR^8R^9$, where $R^5$ is hydrogen, methyl, ethyl, $C_3$ through $C_{20}$ straight or branched chain alkyl, aryl, $OR^{10}$, or $NR^{11}R^{12}$, wherein $R^{10}$ is independently methyl, ethyl, $C_3$ through $C_{20}$ straight or branched chain alkyl, aryl or alkylaryl, $R^{11}$ and $R^{12}$ are independently hydrogen, methyl, ethyl, $C_3$ through $C_{20}$ straight or branched chain alkyl, aryl or alkylaryl, where Y is O, OC(O), $NR^{13}$, or $NR^{14}C(O)$, and where $R^6$, $R^7$, $R^8$, $R^9$, $R^{13}$, and $R^{14}$ are independently hydrogen, methyl, ethyl, $C_3$ through $C_{20}$ straight or branched chain alkyl, aryl, or alkylaryl.

DETAILED DESCRIPTION OF THE INVENTION

A method for preparing ester substituted dihydroxypyrroles begins with providing a nitrogen triester, $N(CH_2C(O)OR)_3$, and converting the nitrogen triester into an ester substituted dihydroxypyrrole using a condensation reaction. The condensation reaction is preferably a modified Hinsberg condensation reaction. Hinsberg condensation refers to a published reaction (Hinsberg *Chem. Ber.* 1910, 43, 901) involving the condensation of diethyl oxalate and the diethyl thiodiglycolate acid in ethanol with sodium ethoxide. Traditionally, and as used herein, any condensation of a derivative of tlhiodiglycolic acid (in which the sulfur is substituted by another heteroatom) with diethyl oxalate to yield the 3,4-dihydroxyheterocycle has been referred to as a Hinsberg condensation. The ester substituted dihydroxypyrroles can be annulated to form a second ring including oxygens from the dihydroxy of the ester substituted dihydroxypyrrole to form an ester substituted alkylenedioxypyrrole. Saponification of the ester substituted alkylenedioxypyrrole followed by neutralization and decarboxylation of the acid substituted alkylenedioxypyrrole results in the formation of an 3,4-alkylenedioxypyrrole N-acetic acid. Subsequently the 3,4-alkylenedioxypyrrole N-acetic acid can be converted from a variety of N-substituted 3,4-alkylenedioxypyrrole that can be polymerized to conjugated polymers.

The nitrogen triester, $N(CH_2C(O)OR)_3$, where the three R groups are independently hydrogen, methyl, ethyl, $C_3$ through $C_{20}$ straight or branched chain alkyl, or aryl, can be either synthesized or obtained commercially. In one preferred embodiment, the R groups are the same. In another embodiment, the nitrogen triester includes different R groups. Different ester groups can provide certain triester properties, such as allowing for selective hydrolysis. One exemplary synthesis route to the triethyl triester is esterification of commercially available nitrilotriacetic acid trisodium salt with sulfuric acid and ethanol in quantitative yields. The nitrogen triester has the following structure:

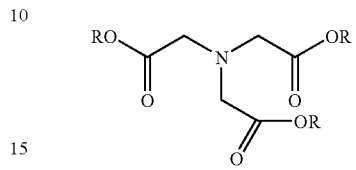

The nitrogen triester can then be converted into an ester substituted dihydroxypyrrole via a Hinsberg condensation reaction with diethyl oxalate catalyzed by $M^+OR^-$ in ROH, where M=an alkali metal and R=alkyl, aryl, functional alkyl, or functional aryl, (89% for M=Na, R=Et) to form a dihydroxypyrrole of the structure:

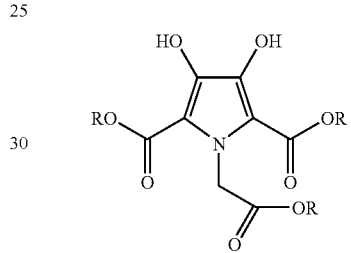

where $R^1$, $R^2$, and $R^3$ are independently alkyl, aryl, functional alkyl, or functional aryl groups. The dihydroxypyrrole can be isolated in high yield by simple treatment with aqueous acid, to generate the protonated form, followed by vacuum filtration. Further purification can be achieved by simple water washing and drying of the solid.

A preferred starting compound, triethyl nitrilotriacetate, is commercially available in small quantities but is easily prepared in nearly quantitative yield starting from commercially available nitrilotriacetic acid or its mono-, di-, or tri-basic salt, of which the free acid and the trisodium salt are commercially available in bulk. The triacid or its salt is converted to a triester that can be isolated by distillation. Other more complex triesters can be prepared, for example, by appropriately reacting triethyl nitrilotriacetate under stoichiometrically controlled transesterification reaction conditions.

The next step of the reaction sequence involves annulating the dihydroxypyrrole. This can be carried out by a Williamson etherification reaction with a disubstituted alkyl chain of the structure, $X(CHR^1)_m(CR^2R^3)_n(CHR^4)_{p-m-n}X$ where X is Cl, Br, or I, a sulfate, or a sulfonate, p is 2 to 6, m is 1 to p−1, and n is 0 to p−2 and $R^1$, $R^2$, $R^3$ and $R^4$ are independently hydrogen, methyl, ethyl, $C_3$ through $C_{20}$ straight or branched chain alkyl, aryl, or alkylaryl. Alternately the annulation may be carried out via a Mitsunobu reaction between the dihydroxypyrrole and a diol of the structure $HO(CHR^1)_m(CR^2R^3)_n(CHR^4)_{p-m-n}OH$ where p is 2 to 6, n is 1 to p−1, and m is 0 to p−2 and $R^1$, $R^2$, $R^3$ and $R^4$ are independently hydrogen, methyl, ethyl, $C_3$ through $C_{20}$ straight or branched chain alkyl, aryl, or alkylaryl. The annulation product is given by the structure:

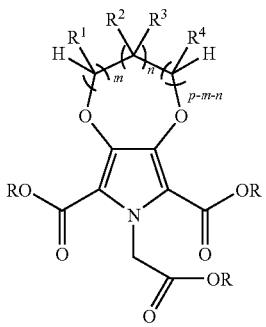

where $R^1$, $R^2$, $R^3$, $R^4$, m, n, and p are defined as before and $R^4$, $R^5$, and $R^6$ are independently alkyl, aryl, functional alkyl, or functional aryl groups. This product can be isolated by washing with water followed by recrystallization in a solvent such as methanol, ethanol, acetone, or ethyl acetate.

The next transformation step of the process is to convert the annulated product to the desired 3,4-alkylenedioxypyrrole-acetic acid. This can be carried out by the saponification of the ester groups of the annulated product and the subsequent decarboxylation to 3,4-alkylenedioxypyrrole-acetic acid. This is carried out by the sequential addition of an aqueous solution of a base and neutralization of the basic solution with an acid to form a triacid. The decarboxylation of this triacid spontaneously occurs upon heating, generally to a temperature greater than 140° C. but less than 200° C. A heat transfer agent, such as numeral oil or a hot inert gas, such as nitrogen or argon, may be included. The 3,4-alkylenedioxypyrrole-acetic acid is given by the structure:

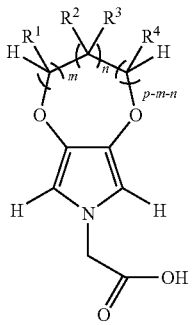

where $R^1$, $R^2$, $R^3$, $R^4$, m, n, n, and p are defined as previously for the adulated product. The 3,4-alkylenedioxypyrrole-acetic acid thus formed in high yield is easily purified by recrystallization.

Figure 2:
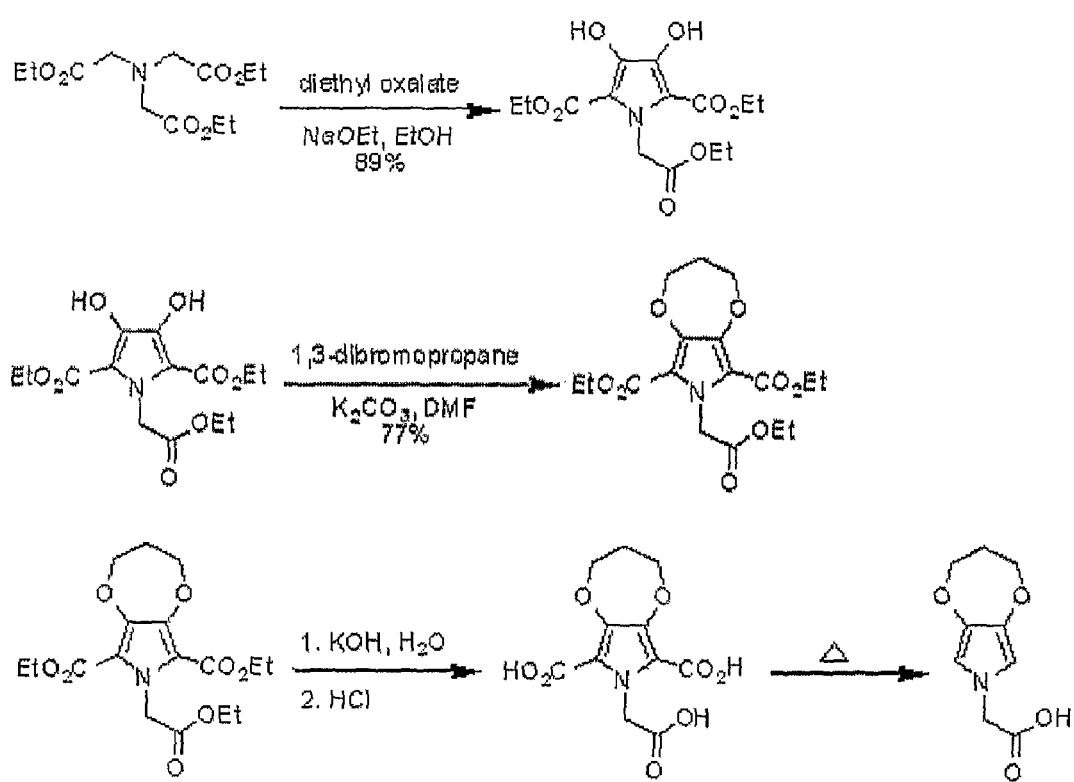
FIG. 2 shows an exemplary method according to the invention for forming 3,4-propylenedioxypyrrole-acetic acid.
Figure 3:
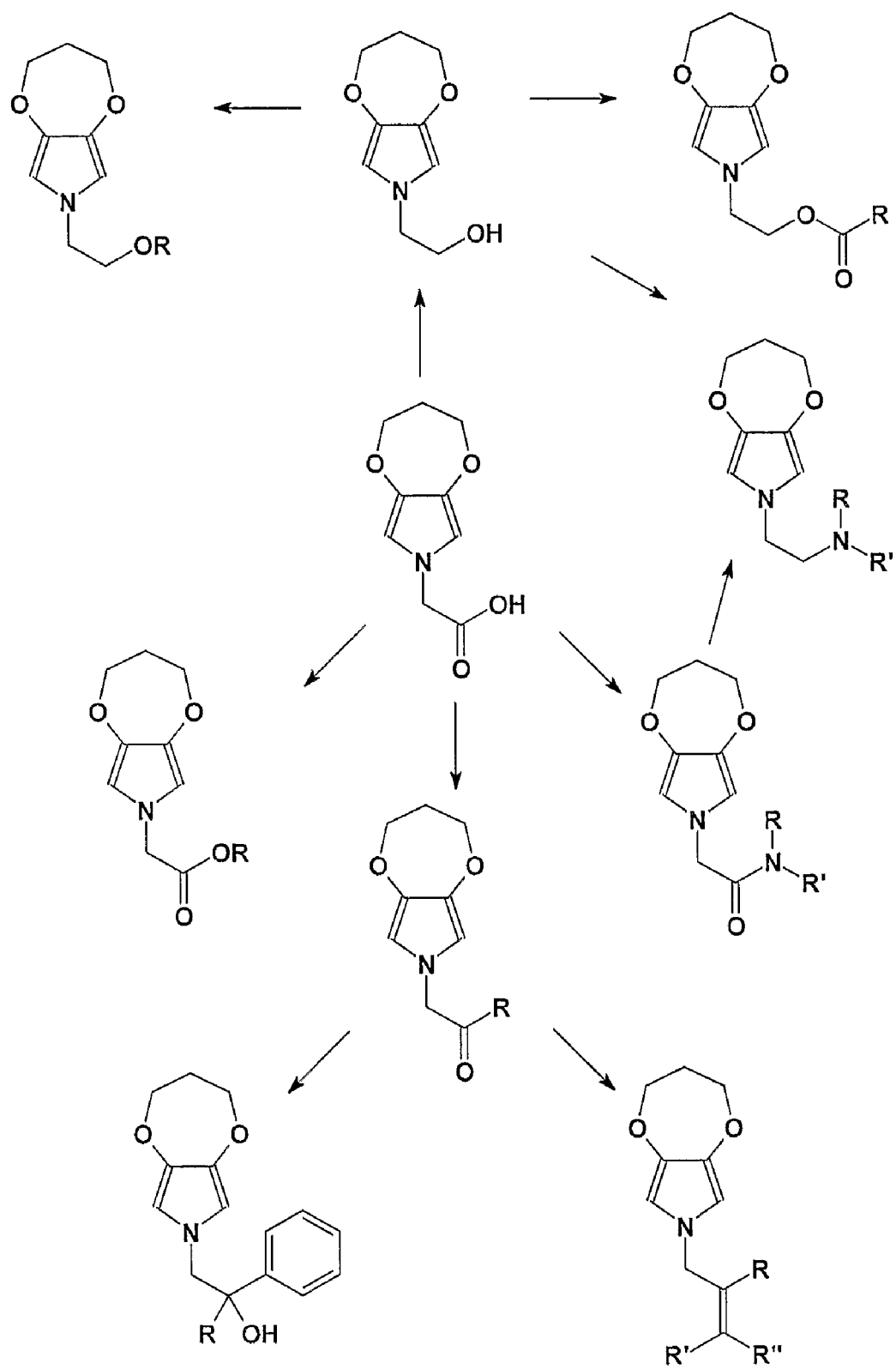
FIG. 3 shows the product matrix possible by the conversion of 3,4-propylenedioxypyrrole-acetic acid into various functional derivatives and subsequent conversion of these derivatives into additional derivatives according to various embodiments or the invention.

The overall process is illustrated in FIG. 2 in a non-limiting example for the preparation of 3,4-propylenedioxypyrrole-acetic acid. The 3,4-alkylenedioxypyrrole-acetic acid once isolated can be further converted to other N-substituted 3,4-alkylenedioxypyrroles by the transformation of the acid group to other functionality including an alcohol, an aldehyde, various ketones, esters, and amides which can subsequently be transformed into amines, ethers, esters, olefins and other functional compounds with an N-methylene or ethylene 3,4-alkylenedioxypyrrole unit connected to these functional groups. The partial scope of compounds which can be prepared from the acid intermediate is illustrated in FIG. 3 where the R groups can be any substituted or unsubstituted alkyl, allyl aryl, or aryl group. Such transformations are known by those of ordinary skill in the art of organic synthesis. For example, the conversion from the acid to esters and amides may be carried out by traditional methods for the condensation of acids with alcohols or amines, respectively. The reduction of the acid to in alcohol can be carried out and subsequently it can be used as an intermediate for further functionalization of the N-substituted 3,4-alkylenedioxypyrrole. Amides formed from the 3,4-alkylenedioxypyrrole-acetic acids can be reduced to amines and the amines used for further functionalization of the N-substituted 3,4-alkylenedioxypyrrole. Specific non-limiting examples are shown in FIGS. 4(a) and (b) for the conversion of 3,4-propylenedioxypyrrole-acetic acid to an ester, and to an alcohol and its subsequent conversion to an ether, respectively.

The inventive 3,4-alkylenedioxypyrroles with N-acetic acid derivatives are not limited to preparation via the Hinsberg condensation reactions to form ester substituted dihydroxypyrroles. For example, one alternative to a Hinsberg condensation for forming the substituted dihydroxypyrrole is a transetherification reaction, shown in FIG. 5, for forming the allylene bridge with the N-acetic acid moiety. FIG. 6 shows another alternative synthesis for forming an ester substituted dihydroxypyrroles.

The invention is a new facile and efficient route towards ester substituted dihydroxypyrroles and to N-substituted 3,4-alkylenedioxypyrroles that use inexpensive and environmentally benign reagents. An addition advantage of the inventive synthesis is that it does not require the use of chromatography, a major expense on an industrial scale required by existing processes for isolating N-alkylated 3,4-alkylenedioxypyrroles. The compound, 3,4-alkylenedioxypyrrole-acetic acid is a versatile intermediate where the acid can be converted to a wide variety of functional groups, including esters, amides, amines, ethers, alcohols, and olefins. This synthetic flexibility of the intermediate combined with its stable storage properties and its ease of purification makes the invention well suited for the exploration and commercialization of new materials. The invention provides a route to numerous novel compositions of matter. The intermediate 3,4-alkylenedioxypyrrole-acetic acids and many functional monomers that can be prepared from these intermediates are novel compositions of matter. The conjugated polymers can be prepared with degrees of polymerization between 4 and 1,000. The conjugated polymers from these monomers are novel compositions of matter that are potentially useful for electrochromic windows, mirrors and displays, electronic paper, anti-stat conductors, transparent conductors, field effect transistors, supercapacitors, batteries, photovoltaic devices, and other electronic components due to their elevated band gaps, low oxidation potentials, and potential biological activity.

EXAMPLES

It should be understood that the examples of synthetic methodology, intermediates, monomeric N-substituted 3,4-alkylenedioxypyrroles, and polymers from these monomers described below are provided for illustrative purposes only and do not in any way limit the scope of the invention.

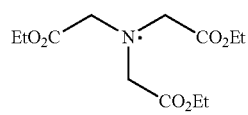

Triethyl Nitrilotriacetate

To a 1000-mL round bottom flask containing a stir bar, an argon atmosphere, and outfitted with a reflux condenser, was added nitrilotriacetic acid (50.00 g, 262 mmol), ethanol (200 proof, 500 mL), and sulfuric acid (concentrated, 15 mL). The mixture was refluxed for 3 hours, cooled to room temperature, and concentrated in vacuo. The concentrate was immediately dissolved into dichloromethane (DCM) (300 mL) and washed with small portions of saturated sodium bicarbonate until the evolution of gas ceased. The solvent was removed, and the resulting concentrated liquid was distilled (bp 135° C. @ 0.1 mmHg) to yield 56.61 g (79%) of a clear oil. $^1$H NMR (300 MHz, CDCl$_3$): δ 4.13 (q, 6H, J=8.0 Hz), 3.62 (s, 6H), 1.23 (t, 9H, J=8.0 Hz); $^{13}$C NMR (75 MHz, CDCl$_3$): δ 170.9, 60.8, 55.3, 14.3; HRMS (EI): Calcd for C$_{12}$H$_{21}$NO$_6$ ([M]$^+$), 275.1369, found m/z, 275.1364; Anal. Calcd for C$_{12}$H$_{21}$NO$_6$: C, 52.35; H, 7.69; N, 5.09%, found: C, 52.11; H, 7.84; N, 5.37%.

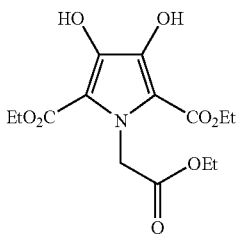

Diethyl 1-(2-ethoxy-2-oxoethyl)-3,4-dihydroxy-1H-pyrrole-2,5-dicarboxylate

To a 1000-mL round bottom flask was added containing a stir bar, and argon atmosphere, and outfitted with a reflux condenser was added ethanol (200 proof, 500 mL) and sodium metal (21.31 g, 927 mmol). When the sodium was completely dissolved, a mixture of triethyl nitrilotriacetate (56.20 g, 204 mmol) and diethyl oxalate (29.44 g, 204 mmol) was added. The mixture was refluxed overnight, whereupon it became a clear, gelatinous solution. After cooling to room temperature, the mixture was poured into 1200 mL of DI water, chilled in an ice bath and acidified with glacial acetic acid (200 mL). The resulting white precipitate was isolated via vacuum filtration and washed with several portions of DI water to yield 59.75 g (89%) of a white solid. mp 121.3-121.8° C.; $^1$H NMR (300 MHz, CDCl$_3$): δ 7.51 (s, 2H), 5.32 (s, 2H), 4.39 (q, 4H, J=7.7 Hz), 4.20 (q, 2H, J=7.7 Hz), 1.38 (t, 6H, J=7.7 Hz), 1.27 (t, 3H, J=7.7 Hz); $^{13}$C NMR (75 MHz, CDCl$_3$): δ 169.5, 162.4, 139.6, 111.1, 61.6, 47.9, 14.5, 14.4; HRMS (EI): Calcd for C$_{14}$H$_{19}$NO$_8$ ([M]$^+$), 329.1111, found m/z, 329.1111; Anal. Calcd for C$_{14}$H$_{19}$NO$_8$: C, 51.06; H, 5.82; N, 4.25%, found: C, 50.79; H, 5.83; N, 4.22%.

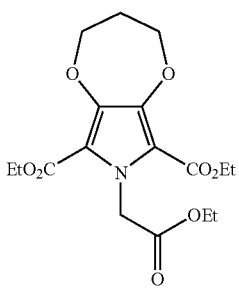

Diethyl 7-(2-ethoxy-2-oxoethyl)-2,3,4,7-tetrahydro-[1,4]dioxepino[2,3-c]pyrrole-6,8-dicarboxylate To a 500-mL round-bottom flask containing a stir bar and an argon atmosphere was added diethyl 1-(2-ethoxy-2-oxoethyl)-3,4-dihydroxy-1H-pyrrole-2,5-dicarboxylate (48.00 g, 146 mmol), 1,3-dibromopropane (29.48 g, 146 mmol), anhydrous potassium carbonate (50.36 g, 364 mmol), and anhydrous dimethylformamide (DMF) (250 mL). The reaction was heated to 105° C. and became lime green after about 30 minutes. The reaction was stirred for 12 hours, during which, it became yellow, and was cooled to room temperature. The mixture was poured into DI water (500 mL), the solids were collected via vacuum filtration, and washed with several portions of DI water. The solids were recrystallized from hot methanol to yield 44.90 g (80%) of a yellow solid. mp 139.7-139.9° C.; $^1$H NMR (300 MHz, CDCl$_3$): δ 5.43 (s, 2H), 4.30 (q, 4H, J=7.7 Hz), 4.22 (q, 2H, J=8.0 Hz), 4.20 (t, 6H, J=63 Hz), 2.25 (p, 2H, J=6.3 Hz), 1.34 (t, 6H, J=7.7 Hz), 1.28 (t, 3H, J=8.0 Hz); $^{13}$C NMR (75 MHz, CDCl$_3$): δ 169.6, 161.0, 142.7, 114.1, 71.7, 61.5, 60.9, 48.0, 33.4, 14.5, 14.4; HRMS (EI): Calcd for C$_{17}$H$_{23}$NO$_8$ ([M]$^+$), 369.1424, found m/z, 369.1417; Anal. Calcd for C$_{17}$H$_{23}$NO$_8$: C, 55.28; H$_3$, 6.28; N, 3.79%, found: C, 55.29; H, 6.37; N, 3.80

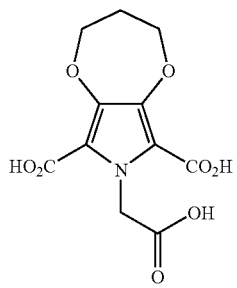

7-(carboxymethyl)-2,3,4,7-tetrahydro-[1,4]dioxepino[2,3-c]pyrrole-6,8-dicarboxylic acid To a 100-mL round-bottom flask was added diethyl 7-(2-ethoxy-2-oxoethyl)-2,3,4,7-tetrahydro-[1,4]dioxepino[2,3-c]pyrrole-6,8-dicarboxylate (17.56 g, 47.5 mmol), DI water (45 mL), acetone (25 mL), and potassium hydroxide (13.34 g, 238 mmol). The reaction mixture was bubbled with argon for 20 minutes, then refluxed for 2.5 hours, resulting in a deep brown solution. The organic volatiles were removed in vacuo and the remaining aqueous layer was chilled in an ice bath. To the mixture was added concentrated sulfuric acid until a pH of 6 was reached, whereupon a white solid precipitate formed. This precipitate was filtered from the red aqueous solution and washed with several portions of DI water, and after drying weighed 13.55 g (100%). To confirm the structure NMR analysis was performed on the fully deprotonated version by dissolving into a NaOD/D$_2$O solution. $^1$H NMR (300 MHz, D$_2$O/NaOD): δ 5.17 (s, 2H), 4.13-4.09 (m, 4H), 2.19 (p, 2H, J=5.7 Hz). $^{13}$C NMR (75 MHz, CDCl$_3$): δ 180.9, 171.0, 141.9, 120.3, 74, 9, 51.9, 36.3. The product was used in the subsequent reaction without further purification.

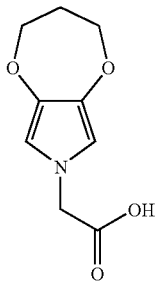

2-(2,3-dihydro-[1,4]dioxepino[2,3-c]pyrrol-7(2H)-yl)acetic acid

To a 250-mL round-bottom flask containing a stir bar and an argon atmosphere was added heavy mineral oil (100 mL). The solution was heated to 80-100° C., where it was deoxygenated with three vacuum/argon purges, after which it was heated to 160° C. While maintaining a continuous argon blanket, 7-(carboxy ethyl)-2,3,4,7-tetrahydro-[1,4]dioxepino[2,3-c]pyrrole-6,8-dicarboxylic acid (13.55 g, 47.5 mmol) was added in small portions. The resulting slurry was stirred for an additional 10 minutes, then cooled to room temperature. Hexanes (250 mL) were added to the flask and decanted. The remaining solids were dissolved in methanol (250 mL), and the solution was filtered to remove trace solids. After removal of the solvent in vacuo, 7.94 g (85%) of a tan solid was isolated. $^1$H NMR (300 MHz, DMSO-d6): δ 6.12 (s, 2H), 3.88 (s, 2H), 3.82 (dd, 4H), 1.97 (p, 2H, J=5.7 Hz); $^{13}$C NMR (75 MHz, DMSO-d6): δ 170.9, 137.4, 106.7, 71.8, 54.4, 35.1; FIRMS (EI): Calcd for $C_9H_{11}NO_4$ ([M]$^+$), 197.0688, found m/z, 197.0687.

Figure 5:
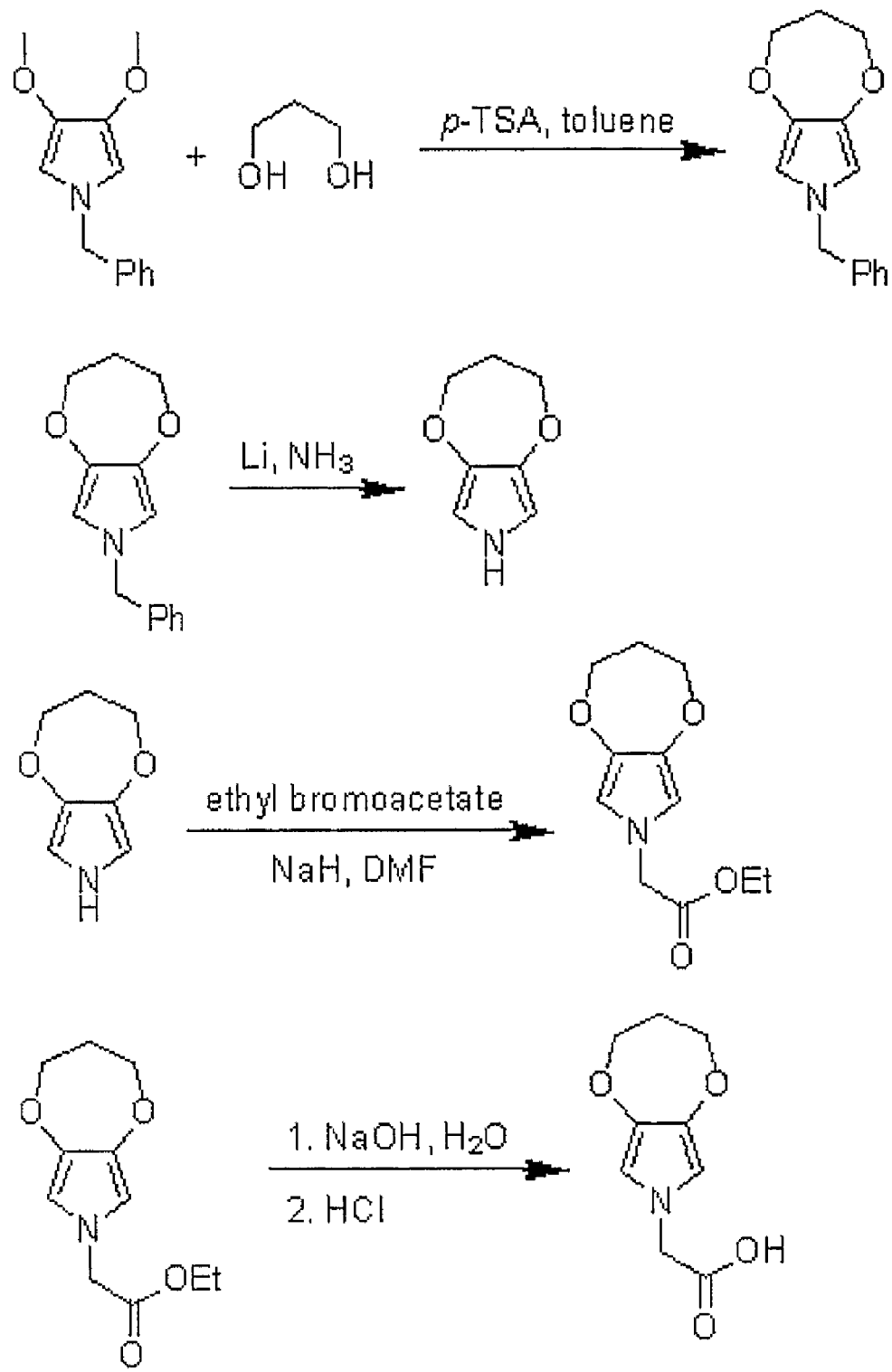
FIG. 5 shows a transetherification reaction for forming the alkylene bridge with the N-acetic acid moiety, according to an embodiment of the invention.
Figure 6:
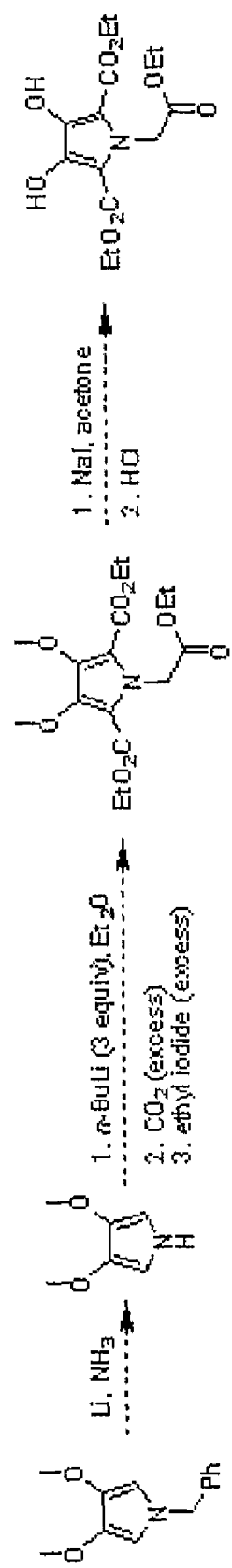
FIG. 6 shows another alternative pathway for forming N-substituted dihydroxypyrroles, according to an embodiment of the invention.

An alternate synthetic route to 2-(2,3-dihydro-[1,4]dioxepino[2,3-c]pyrrol-7(2H)-yl)acetic acid can be carried out by the condensation of 3,4-propylenedioxypyrrole with ethyl bromoacetate under basic conditions in DMF to produce the ethyl ester in moderate yields, as illustrated in the third step of FIG. 5, which can then undergo saponification of the ester and neutralized to yield the desired acid, as illustrated in the fourth step of FIG. 5. This synthetic route is deficient relative to the synthetic route outlined in FIG. 2 due to lower overall yields of preparing the 3,4-propylenedioxypyrrole, which is illustrated by the first six steps of FIG. 1(*a*), where protecting groups must be used in addition to more expensive (e.g. palladium) and toxic catalysts and reagents.

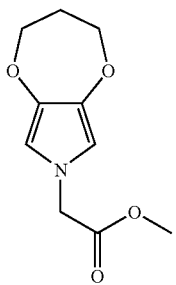

Methyl 2-(3,4-dihydro-[1,4]dioxepino[2,3-c]pyrrol-7(2H)-yl)acetate

To a 50-mL round-bottom flask containing a stir bar and an argon atmosphere was added 2-(2,3-dihydro-[1,4]dioxepino[2,3-c]pyrrol-7(2H)-yl)acetic acid (1.00 g, 5.07 mmol), anhydrous DMF (25 mL), methyl iodide (0.86 g, 6.08 mmol), and anhydrous $K_2CO_3$ (1.05 g, 7.61 mmol). The reaction was heated to 60° C. and stirred for 17 hours, after which it was cooled to room temperature and poured into DI water (250 mL). The resulting mixture was extracted with 2×100 mL ethyl acetate, concentrated in vacuo, flashed through a pad of silica gel (ethyl acetate), and concentrated in vacuo to give 0.60 g (56%) of a white solid. TLC $R_f$=0.24 (Silica Gel, Ethyl Acetate); $^1$H NMR (300 MHz, CDCl$_3$): δ 6.20 (s, 2H), 4.39 (s, 2H), 4.01-3.98 (m, 4H), 3.75 (s, 3H), 2.17-2.10 (m, 2H); $^{13}$C NMR (75 MHz, CDCl$_3$): δ 169.5, 139.7, 107.5, 72.6, 52.7, 51.5, 35.3; HRMS (ESI FTICR): Calcd for $C_{10}H_{14}NO_4$ ([M+H]$^+$), 212.0917, found m/z, 212.0918; Anal. Calcd for $C_{10}H_{13}NO_4$: C, 56.86; H, 6.20; N, 6.63%, found C, 56.13; H, 6.06; N, 6.38%:

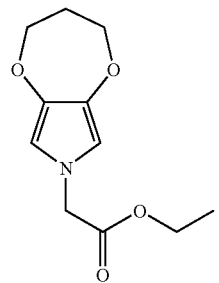

Ethyl 2-(3,4-dihydro-[1,4]dioxepino[2,3-c]pyrrol-7(2H)-yl)acetate

Into a 250 mL round-bottom flask equipped with a magnetic stir bar, a nitrogen inlet adapter, additional funnel and a rubber septum was added 3,4-propylenedioxypyrrole (0.60 g, 4.31 mmol). Anhydrous dimethylformamide (DMF) (40 mL) was then added to the flask and the mixture was cooled to 0° C. NaH (60% in mineral oil, 0.19 g, 4.74 mmol) was added to the solution. The pale yellow slurry was stirred for 2 h at room temperature, followed by addition of ethyl bromoacetate (0.56 mL, 4.74 mmol). The mixture was stirred overnight at room temperature and then DI water (200 mL) was added. The crude compound was extracted with 3×100 mL Et$_2$O and the combined organic extracts were dried over Na$_2$SO$_4$. The solvent was removed in vacuo, giving a reddish oily residue. The compound was purified by column chromatography on silica gel (3:1=Hexanes:Ethyl Acetate) to yield 0.63 g (65%) of a colorless oil. TLC $R_f$=0.78 (Silica Gel, (Ethyl Acetate); $^1$H NMR (300 MHz, CDCl$_3$): δ6.17 (s, 2H), 4.33 (s, 2H), 4.16 (q, 2H, J=7.2 Hz), 3.95 (m, 4H), 2.09 (m, 2H), 1.24 (t, 3H, J=7.2 Hz); $^{13}$C NMR (75 MHz, CDCl$_3$): δ 168.7, 139.4, 107.2, 72.3, 61.4, 51.3, 35.0, 14.0. HRMS (ESI FTICR): Calcd for $C_{11}H_{16}NO_4$ ([M+H]$^+$), 226.1074, found m/z, 226.1071; Anal. Calcd for $C_{11}H_{15}NO_4$: C, 58.66; H, 6.71; N, 6.22%, found: C, 58.44; H, 5.79; N, 6.90%.

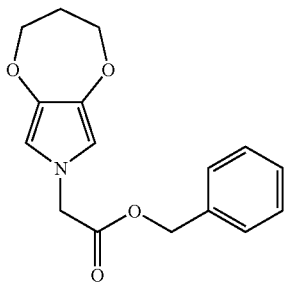

Benzyl 2-(3,4-dihydro-[1,4]dioxepino[2,3-c]pyrrol-7 (2H)-yl)acetate

To a 50-mL round-bottom flask containing a stir bar and an argon atmosphere was added 2-(2,3-dihydro-[1,4]dioxepino [2,3-c]pyrrol-7(2H)-yl)acetic acid (1.00 g, 5.07 mmol), anhydrous DMF (25 mL), benzyl bromide (0.91 g, 5.32 mmol), and anhydrous $K_2CO_3$ (1.05 g, 7.61 mmol). The reaction was heated to 60° C. and stirred for 17 hours, after which it was cooled to room temperature and poured into DI water (250 mL). The resulting precipitate was isolated via vacuum filtration, washed with DI water, and air dried to give 0.70 g (48%) of a white powder. TLC $f_f$=0.81 (Silica Gel, 3:2=Hexanes: $Et_2O$); mp 71.8-72.7° C.; $^1H$ NMR (300 MHz, $CDCl_3$): δ 7.38-7.31 (m, 5H), 6.21 (s, 2H), 5.18 (s, 2H), 4.42 (s, 2H), 4.01-3.98 (m, 4H), 2.17-2.10 (m, 2H); $^{13}C$ NMR (75 MHz, $CDCl_3$): δ 168.9, 139.8, 135.3, 128.9, 128.8, 128.5, 107.5, 72.7, 67.4, 51.7, 35.3; HRMS (ESI FTICR): Calcd for $C_{16}H_{18}NO_4$ ($[M+H]^+$), 288.1230, found m/z, 288.1229; Anal. Calcd for $C_{16}H_{17}NO_4$: C, 66.89; H, 5.96; N, 4.88%, found: C, 66.87; H, 5.93; N, 4.53%.

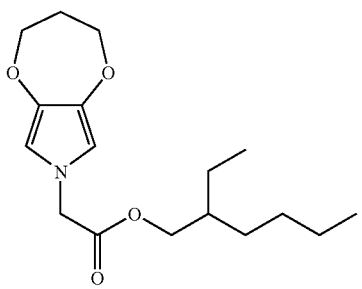

2-Ethylhexyl 2-(3,4-dihydro-[1,4]dioxepino[2,3-c] pyrrol-7(2H)-yl)acetate

To a 100 mL round-bottom flask containing a stir bar and an argon atmosphere was added 2-(2,3-dihydro-[1,4]diox-epino[2,3-c]pyrrol-7(2H)-yl)acetic acid (2.00 g, 10.1 mmol), anhydrous DMF (50 mL), 1-bromo-2-ethylhexane (2.06 g, 10.6 mmol), and anhydrous $K_2CO_3$ (2.10 g, 15.2 mmol). The reaction was heated to 60° C. and stirred for 15 hours. After cooling to room temperature, the mixture was poured into DI water (250 mL) and extracted with 2×100 mL $Et_2O$. The combined organic layers were washed with DI water (100 mL), brine (50 mL), and dried over anhydrous $Na_2SO_4$. The solvent was removed in vacuo, and the concentrate was purified via flash chromatography on silica gel (deactivated with TEA, 7:4=$Et_2O$:Hexanes) to yield 2.65 g (84%) of a clear oil. TLC $R_f$=0.23 (Silica Gel, 3:2=$Et_2O$: Hexanes); $^1H$ NMR (300 MHz, $CDCl_3$): δ 6.19 (s, 2H), 4.36 (s, 2H), 4.04 (dd, 2H, 0.1=6.0 Hz, J=2.0 Hz), 3.99-3.96 (m, 4H), 2.15-2.09 (m, 2H), 1.55 (p, 1H, J=6.3 Hz), 1.43-1.23 (m, 8H), 0.88 (t, 3H, J=7.0 Hz), 0.86 (t, 3H, J=8.3 Hz); $^{13}C$ NMR (75 MHz, $CDCl_3$): δ 169.2, 139.7, 107.5, 72.6, 68.0, 51.7, 38.8, 35.3, 30.4, 29.0, 23.9, 23.1, 14.2, 11.1; HRMS (ESI FTICR): Calcd for $C_{17}H_{28}NO_4$ ($[M+H]^+$), 310.2013, found m/z, 310.2007; Anal. Calcd for $C_{17}H_{27}NO_4$: C, 65.99; H, 8.80; N, 4.53%, found: C, 65.77; H, 8.72; N, 4.43%.

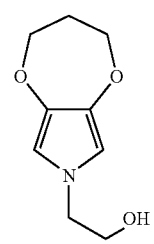

2-(2,3-dihydro-[1,4]dioxepino[2,3-c]pyrrol-7(2H)-yl)ethanol

To a dry 250-mL round-bottom flask containing a stir bar and an argon atmosphere was added 2-(2,3-dihydro-[1,4]di-oxepino[2,3-c]pyrrol-7(2H)-yl)acetic acid (1.50 g, 7.61 mmol), and dry THF (100 mL). The mixture was cooled in a $CO_2$/2-propanol bath and $LiAlH_4$ powder (1.29 g, 34.0 mmol) was carefully added. When gas evolution stopped, the reaction was walked to room temperature and stirred an additional 3 hours. The reaction was quenched first with methanol, then ice, and then a minimal amount of $H_2SO_4$ was added to quench any alumina aggregates. The mixture was extracted with 2×100 mL of $Et_2O$, and the combined organic layers were washed with saturated $NH_4Cl$ and then brine. The solution was dried over $Na_2SO_4$ and concentrated in vacuo and filtered through a silica gel pad (deactivated with triethylamine) with ethyl acetate as the eluent. After removing the ethyl acetate in vacuo, the pure compound was isolated as 0.70 g (50%) of a pale yellow oil TLC $R_f$=0.67 (Silica Gel, ethyl acetate); mp $^1H$ NMR (300 MHz, $CDCl_3$): δ 6.23 (s, 2H), 3.97 (dd, 4H), 3.78 (br s, 4H), 2.12 (p, 2H, J=5.3 Hz), 1.84 (br s, 1H); $^{13}C$ NMR (75 MHz, $CDCl_3$): δ 139.1, 10.4, 72.6, 62.9, 52.8, 35.3; HRMS (EI): Calcd for $C_9H_{13}NO_3$ ($[M]^+$), 183.0895, found m/z, 183.0892; Anal. Calcd for $C_9H_{13}NO_3$: C, 59.00; H, 7.15; N, 7.65%, found: C, 58.76; H, 7.45; N, 7.35%.

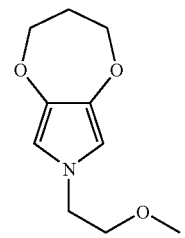

7-(2-Methoxyethyl)-2,3,4,7-tetrahydro-[1,4]dioxepino[2,3-c]pyrrole

To a 50-mL round-bottom flask containing a stir bar and an argon atmosphere was added 2-(2,3-dihydro-[1,4]dioxepino[2,3-c]pyrrol-7(2H)-yl)ethanol (0.50 g, 2.73 mmol), methyl iodide (0.47 g, 3.28 mmol), and anhydrous DMF (25 mL). The mixture was chilled in an ice bath and then sodium hydride (60% dispersion in mineral oil, 0.22 g, 5.46 mmol) was added. The reaction was stirred for 15 hours, during which the ice bath was allowed to warm to room temperature. The mixture was then poured into DI water (100 mL), and extracted with 2×50 mL Et$_2$O. The organic layers were combined, washed with brine, dried over Na$_2$SO$_4$, and concentrated in vacuo. The residue was purified via flash chromatography on silica gel (deactivated with TEA, 5:6=Hexanes:Et$_2$O) to yield 0.42 g (78%) of a clear oil. TLC R$_f$=0.24 (Silica Gel, 1:1=Hexanes:Et$_2$O); $^1$H NMR (300 MHz, CDCl$_3$): δ 6.21 (s, 2H), 3.97-3.93 (m, 4H), 3.78 (t, 2H, J=6.3 Hz), 3.55 (t, 2H, J=6.0 Hz), 3.30 (s, 3H), 2.13-2.06 (m, 2H); $^{13}$C NMR (75 MHz, CDCl$_3$): δ 138.9, 106.5, 72.64, 72.58, 59.2, 50.2, 35.4; HRMS (ESI FTICR): Calcd for C$_{10}$H$_{16}$NO$_3$ ([M+H]$^+$), 198.1130, found m/z, 198.1120; Anal. Calcd for C$_{10}$H$_{15}$NO$_3$: C, 60.90; H, 7.67; N, 7.10%, found: C, 61.08; H, 7.64%; N, 7.10%.

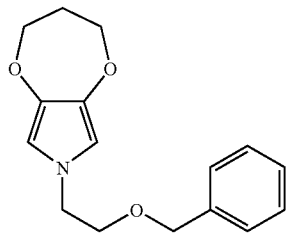

7-(2-(Benzyloxy)ethyl)-2,3,4,7-tetrahydro-[1,4]dioxepino[2,3-c]pyrrole

To a 50-mL round-bottom flask containing a stir bar and an argon atmosphere was added 2-(2,3-dihydro-[1,4]dioxepino[2,3-c]pyrrol-7(2H)-yl)ethanol (0.50 g, 2.73 mmol), benzyl bromide (0.56 g, 3.28 mmol), and anhydrous DMF (25 mL). The mixture was chilled in an ice bath and then sodium hydride (60% dispersion in mineral oil, 0.22 g, 5.46 mmol) was added. The reaction was stirred for 15 hours, during which the ice bath was allowed to warm to room temperature. The mixture was then poured into DI water (100 mL), and extracted with 2×50 mL Et$_2$O. The organic layers were combined, washed with brine, dried over Na$_2$SO$_4$, and concentrated in vacuo. The residue was purified via flash chromatography on silica gel (2:1=Hexanes:Et$_2$O) to yield 0.52 g (64%) of a clear oil. TLC R$_f$=0.28 (Silica Gel, 1:1=Hexanes:Et$_2$O); $^1$H NMR (300 MHz, CDCl$_3$): δ 7.36-7.25 (m, 4H), 6.25 (s, 2H), 4.47 (s, 2H), 4.00-3.97 (m, 4H), 3.84 (t, 2H, J=6.0 Hz), 3.66 (t, 2H, J=5.7 Hz), 2.16-2.10 (m, 2H); $^{13}$C NMR (75 MHz, CDCl$_3$): δ 138.9, 138.1, 128.6, 127.9, 127.8, 73.4, 72.7, 70.2, 50.4, 35.4; HRMS (ESI FTICR): Calcd for C$_{16}$H$_{20}$NO$_3$ ([M+H]$^+$), 274.1443, found m/z, 274.1433; Anal. Calcd for C$_{16}$H$_1$NO$_3$: C, 70.31; H, 7.01; N, 5.12%, found: C, 69.61; H, 6.94; N, 5.00%.

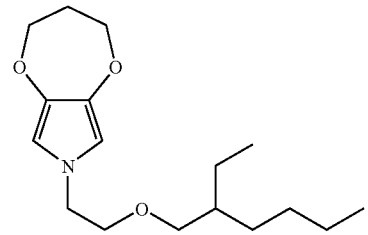

7-(2-(2-Ethylhexyloxy)ethyl)-2,3,4,7-tetrahydro-[1,4]dioxepino[2,3-c]pyrrole To a 50-mL round-bottom flask containing a stir bar and an argon atmosphere was added 2-(2,3-dihydro-[1,4]dioxepino[2,3-c]pyrrol-7(2H)-yl)ethanol (0.41 g, 2.24 mmol), 2-ethylhexyl tosylate (0.77 g, 2.69 mmol), and anhydrous DMF (25 mL). The mixture was chilled in an ice bath and then sodium hydride (60% dispersion in mineral oil, 0.18 g, 4.48 mmol) was added. The reaction was stirred for 15 hours, during which the ice bath was allowed to warm to room temperature. The mixture was then poured into DI water (100 mL), and extracted with 2×50 mL Et$_2$O. The organic layers were combined, washed with brine, dried over Na$_2$SO$_4$, and concentrated in vacuo. The residue was purified via flash chromatography on silica gel (deactivated with TEA, 5:1=Hexanes:Et$_2$O) to yield 0.42 g (64%) of a clear oil. TLC R$_f$=0.46 (Silica Gel, 1:1=Hexanes:Et$_2$O); $^1$H NMR (300 MHz, CDCl$_3$): δ 6.23 (s, 2H), 3.98-3.95 (m, 4H), 3.79 (t, 2H, J=6.0 Hz), 3.58 (t, 2H, J=6.0 Hz), 3.26 (d, 2H, 6.3 Hz), 2.15-2.08 (m, 2H), 1.47 (p, 1H, J=6.7 Hz), 1.35-1.20 (m, 8H), 0.89 (t, 3H, J=7.3 Hz), 0.84 (t, 3H, J=8.3 Hz); $^{13}$C NMR (75 MHz, CDCl$_3$): δ 138.8, 106.5, 74.3, 72.6, 71.1, 50.4, 39.8, 35.4, 30.7, 29.3, 24.0, 23.2, 14.3, 11.3; HRMS (ESI FTICR): Calcd for C$_{17}$H$_{30}$NO$_3$ ([M+H]$^+$), 296.2225, found m/z, 296.2216; Anal. Calcd for C$_{17}$H$_{29}$NO$_3$: C, 69.12; H, 9.89; N, 4.74%, found: C, 68.85; H, 9.75; N, 4.75%.

Poly(N-substituted 3,4-propylenedioxypyrrole)s

The monomers synthesized as above from 2-(2,3-dihydro-[1,4]dioxepino[2,3-c]pyrrol-7(2H)-yl)acetic acid yield materials with different electrochemical and optical properties in their polymeric form. Polymers with degrees of polymerization of four or more begin to display desirable properties. Polymers of high molecular can be formed for many of these monomers, even to a degree of polymerization approaching 1,000. The ability to polymerize the monomers and achieve the desired properties is demonstrated for polymers prepared from the ester monomers whose synthesis and isolations are described above with methyl, ethyl, benzyl, and 2-ethylhexyl substituents that become the polymer's pendant groups. The methyl and ethyl groups contribute minimally towards the overall polarity, steric hindrance of oxidative coupling and disturbance of the conjugated polymers π-stacking interactions, and polymer solubility, while the benzyl group adds a degree of steric hindrance to the molecule and a potential means to π-stacking. The racemic 2-ethylhexyl group is a hydrophobic moiety that can boost the monomer and polymer solubility and possibly disturb polymer π-stacking interactions.

Figure 7:
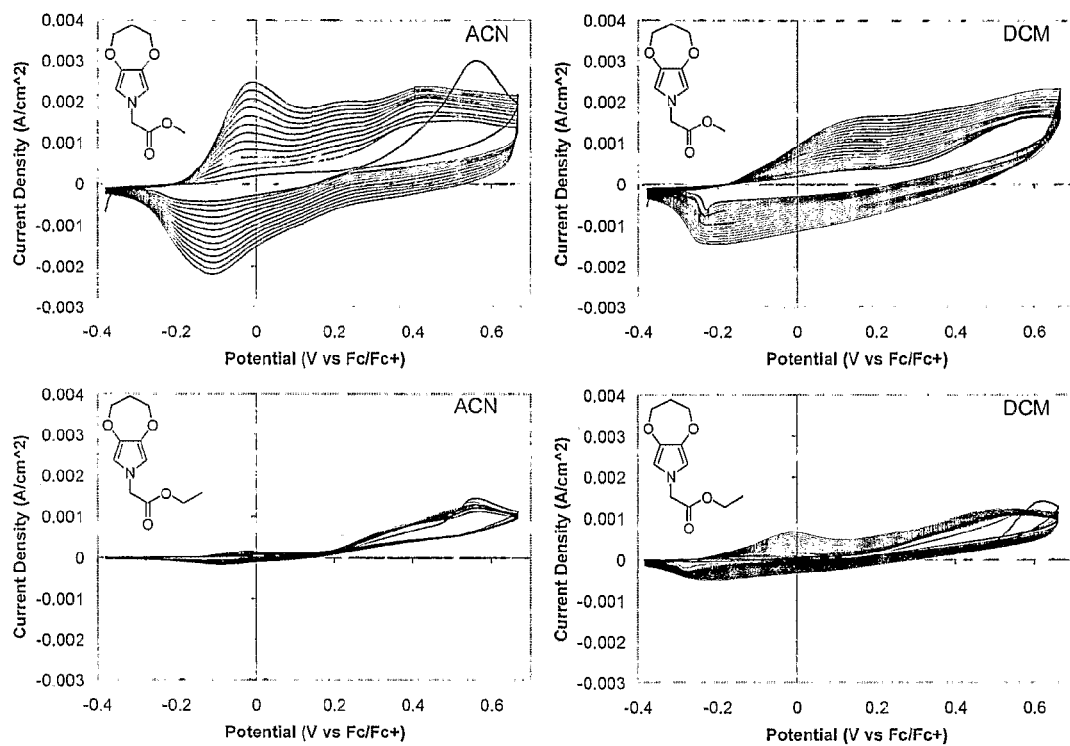
FIG. 7 shows voltamograms of stacked plots of 20 scans at a scan rate of 50 mV/sec for the electropolymerization of two N-acetyl ester substituted 3,4-propylenedioxypyrroles in acetonitrile (left) and dichloromethane (right).

Monomer solutions of similar concentrations in various solvent-supporting electrolyte media were prepared for the four esters indicated above. The solutions were subjected to repeated scanning electropolymerization with a Pt button working electrode, which is a common method for the synthesis of electroactive polymer thin films. The polymers were characterized electrochemically. The potential window that was used for the experiments was chosen by setting the anodic vertex at a voltage in the diffusion tail, just positive of the peak monomer oxidation potential and setting the cathodic vertex at a potential just negative enough to include the entire polymer redox oxidation and reduction waves. As shown in FIG. 7, an irreversible oxidation process is observed at positive potentials when scanning from negative to positive. This can be attributed to the generation of monomer radical cations followed by coupling, which effectively deposits a film of oxidized polymer onto the electrode surface. Upon reverse scanning, a reduction wave is observed, and can be attributed to the conversion of the oxidized (doped) polymer film to its unoxidized (undoped) state. When the neutral (undoped) polymer is then scanned from negative to positive potentials, an oxidation wave is observed at lower potentials than that of the monomer and can be attributed to the conversion of the neutral polymer to its oxidized (doped) state.

Table 1 summarizes the electrochemical data for the monomers and their respective polymers in various electrochemical media. The monomer structure and polymerization medium have a strong effect on the results obtained. As a means of evaluating deposition efficiency of the electroactive polymer film, the $I_{p,ox}^{20}/I_{p,m}^{0}$ value reported in Table 1, which is equal to the ratio of the polymer peak oxidation potential after 20 CV depositions to the first-scan monomer peak oxidation potential, provides a rough numerical value interpretation of the success of electrochemical polymerization where higher values represent more successful polymerizations and is independent of systematic error caused by slightly different concentrations and variation of electrode surface area due to polishing technique. The methyl ester polymerized very well in both acetonitrile ($I_{p,ox}^{20}/I_{p,m}^{0}$=0.82) and dichloromethane ($I_{p,ox}^{20}/I_{p,m}^{0}$=1.02), whereas the ethyl ester polymerized sufficiently in dichloromethane ($I_{p,ox}^{20}/I_{p,m}^{0}$=0.46), but to a much lesser extent in acetonitrile ($I_{p,ox}^{20}/I_{p,m}^{0}$=0.11). This difference in the electrochemical depositions is surprising as the extension of the ester substituent by a single $CH_2$ unit produces a significant difference in the polymerization behavior that consistently occurred upon multiple separate polymerizations. The data in FIG. 7 suggests that solubility differences are responsible for these different extents of polymerization.

TABLE 1

Electrochemical Data of the Various N-substituted 3,4-Propylenedioxypyrrol Derivatives

| N-Substituent | Solvent[a] | $C^*_m$[b] | $E_{p,m}$[c] | $E_{1/2,p}$[d] | $\Delta E_p$[e] | $I_{p,ox}^{20}/I_{p,m}^{0}$[f] | HOMO[g] |
|---|---|---|---|---|---|---|---|
| Acetic Acid[h] | $H_2O$ | 11.8 | 0.48 | — | — | — | — |
| Methyl Ester | DCM | 11.2 | 0.63 | 0.01 | 0.38 | 1.02 | — |
| Methyl Ester | ACN | 12.1 | 0.57 | −0.06 | 0.09 | 0.82 | 4.84 |
| Benzyl Ester | ACN | 10.3 | 0.61 | −0.04 | 0.08 | 0.53 | 4.86 |
| 2-Ethylhexyl Ester | ACN | 10.8 | 0.67 | −0.09 | 0.05 | 0.97 | 4.85 |
| Ethyl Ester | DCM | 10.3 | 0.63 | −0.09 | 0.19 | 0.46 | 4.75 |
| Ethyl Ester | ACN | 10.3 | 0.58 | −0.04 | 0.07 | 0.11 | 4.77 |
| Alcohol | PC[i] | 7.26 | 0.51 | −0.01 | 0.09 | — | — |
| Alcohol | DCM[j] | 11.4 | 0.52 | — | — | — | — |
| Methyl Ether | DCM | 11.0 | 0.53 | −0.21 | 0.02 | 0.17 | 4.76 |
| Methyl Ether | ACN | 10.5 | 0.51 | −0.07 | 0.07 | 0.16 | 4.84 |
| Benzyl Ether | DCM | 12.0 | 0.52 | −0.24 | 0.03 | 0.26 | 4.73 |
| Benzyl Ether | ACN | 11.2 | 0.51 | −0.14 | 0.03 | 0.07 | 4.86 |
| 2-Ethylhexyl Ether | PC | 11.6 | 0.54 | −0.11 | 0.02 | 0.47 | 4.89 |
| 2-Ethylhexyl Ether | ACN | 10.3 | 0.51 | −0.14 | 0.01 | 0.22 | 4.85 |

[a]The solvent for the subsequently reported data. Supporting electrolytes for the solvents: ACN, TBAP; DCM, TBAPF$_6$; PC, LiClO$_4$; H$_2$O, KCl.
[b]Bulk monomer concentration (mM).
[c]Monomer peak oxidation potential (mV vs. Fc/Fc$^+$) at 50 mV/s.
[d]Polymer half-wave potential (V vs. Fc/Fc$^+$).
[e]Separation of polymer peak oxidation and reduction potentials (V).
[f]Ratio of polymer oxidation peak current, after 20 deposition scans, to the initial peak monomer oxidation potential. This value is used as a very rough gauge to determine the success of the electropolymerization.
[g]HOMO (eV) of the neutral polymer as determined by DPV. Values obtained by the assumption that the Fc/Fc$^+$ redox couple resides at 5.12 eV.
[h]Would not electropolymerize in any compatible solvents.
[i]Polymerized galvanostatically at 50 μC to 0.51 V.
[j]Large shifts in potentials were observed, producing unreliable data.

Figure 8:
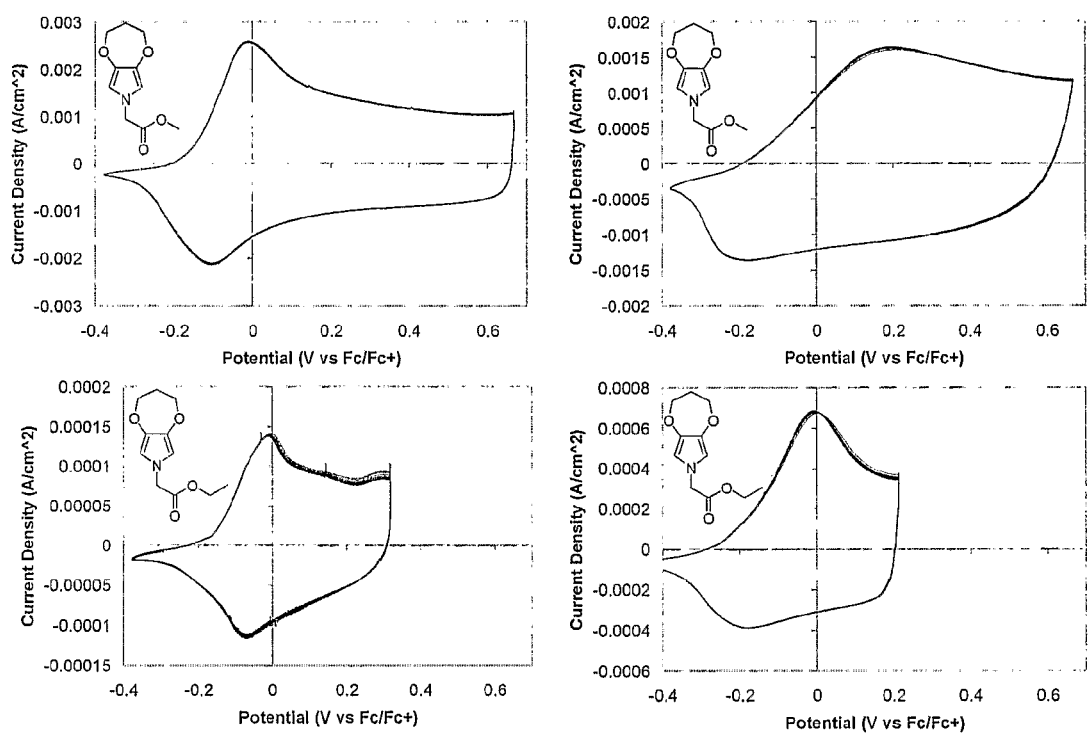
FIG. 8 shows cyclic voltamograms of two monomer free poly(N-acetyl ester substituted 3,4-propylenedioxypyrrole)s in acetonitrile (left) and dichloromethane electrolyte solution (right).

All electrodeposited polymer films were removed from monomer solution, gently rinsed with and immersed in their respective electrolyte solutions. To characterize their redox processes and to determine the stability of the polymer films towards repeated electrochemical decomposition upon switching, as shown in FIG. 8, the films were subjected to several potentiodynamic scans whose switching potentials were chosen as points outside the electrochemical diffusion tails.

In acetonitrile, the redox processes for polymer with the methyl ester and the ethyl ester are well-defined, and the redox peak separation values ($\Delta E_p$=0.09 V and 0.07 mV respectively) are quite low. Furthermore, the $E_{1/2}$ values are very similar ($E_{p,m}$=−0.06 V and −0.04 V respectively), which suggests that the two polymers are very close in electronic structure and that the enhanced electropolymerization of the methyl ester with respect to the ethyl ester in acetonitrile appears to be due to solubility effects. Polymers from the methyl ester and the ethyl ester exhibited different behavior in dichloromethane as the electrochemical solvent. Because dichloromethane is less polar than acetonitrile, it is presumed that the ester pendant groups would exhibit a decreased solubility. The electrochemical process for the two ester polymers is very broad in dichloromethane. A more tightly packed film can possibly hinder ion transport. The redox peak separation values of the polymers from the methyl ester and the ethyl ester ($\Delta E_p$=0.38 V and 0.19 V respectively) are very large for both polymers, and their redox processes are very large. The half wave potentials for the polymers ($\Delta_{1/2}$=0.01 V and −0.09 V respectively) are very different, and upon closer inspection, the $\Delta E_p$ value for the polymer from the methyl ester is almost double that of polymer from the ethyl ester. It is clear that the two polymers have very different morphologies in dichloromethane and that the ethyl group, compared to the methyl group is more compatible with the solvent. These results can be correlated to the difference in polarity of the two monomers; silica gel TLC experiments in ethyl acetate suggest that the methyl ester ($R_F$=0.24) is much more polar than the ethyl ester ($R_F$=0.78).

Figure 9:
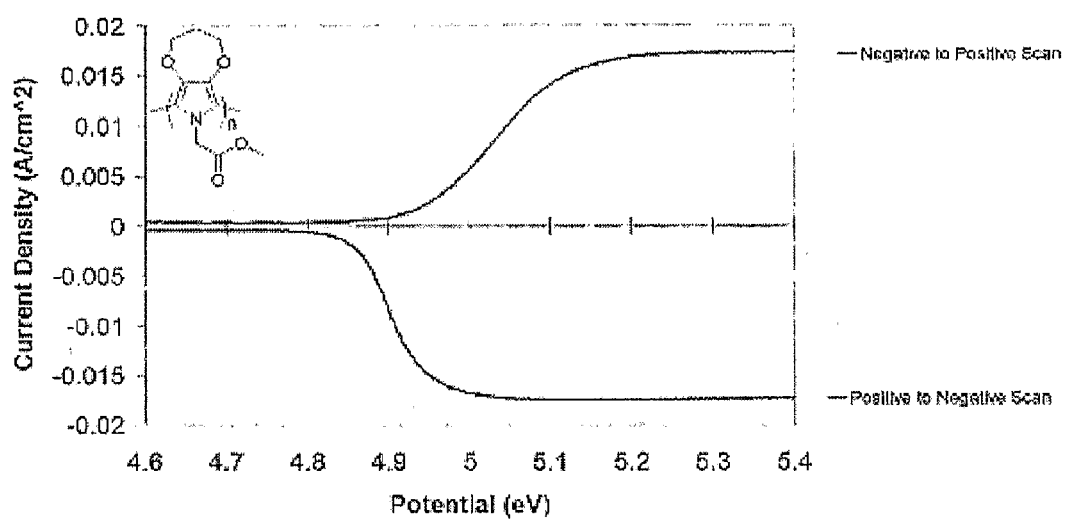
FIG. 9 shows a differential pulse voltamogram of poly(N-(methylacetyl)-3,4-propylenedioxypyrrole) in acetonitrile.

HOMO values were determined by measuring the onset of oxidation in the differential pulse voltammogram (DPV) of the polymer in monomer-free electrolyte solution. This technique is preferred over CV for measuring polymer HOMO levels because the onset of polymer oxidation is more readily apparent due to the elimination of double layer capacitive currents. FIG. 9 illustrates the DPV of the polymer from the methyl ester and the HOMO was measured to exist at 4.84 eV. It can be seen that the HOMO values for all of the polymers fall within the 4.82±0.09 eV range. The closeness of these values is unexpected given the large variability of the other electrochemical properties. Because the HOMO level represents the easiest electron to remove from the system, and originates from polymer chains that undergo the most facile electrochemical switching, its value is most likely independent of the bulk morphological effects observed. It therefore suggests that the diverse fundamental electrochemical processes observed for these materials originates primarily from the morphological effects induced by the various pendant group structures, and not by an inductive or resonance interaction of the pendant group interacting with the conjugated backbone.

The monomers with a Benzyl ester and an ethylhexyl ester were also electropolymerized, and it was found that both depositions occurred readily ($I_{p,ox}^{20}/I_{p,m}^{0}$=0.53 and 0.97 respectively) in acetonitrile. The observed decrease in the propensity for film electrodeposition with increasing ester residue length observed for the ethyl ester with respect to the methyl ester does not continue upon lengthening of the chain, as the benzyl group, which contains seven carbon atoms, and the ethylhexyl group, which contains eight carbon atoms more readily polymerize in acetonitrile than did the ethyl ester.

Figure 10:
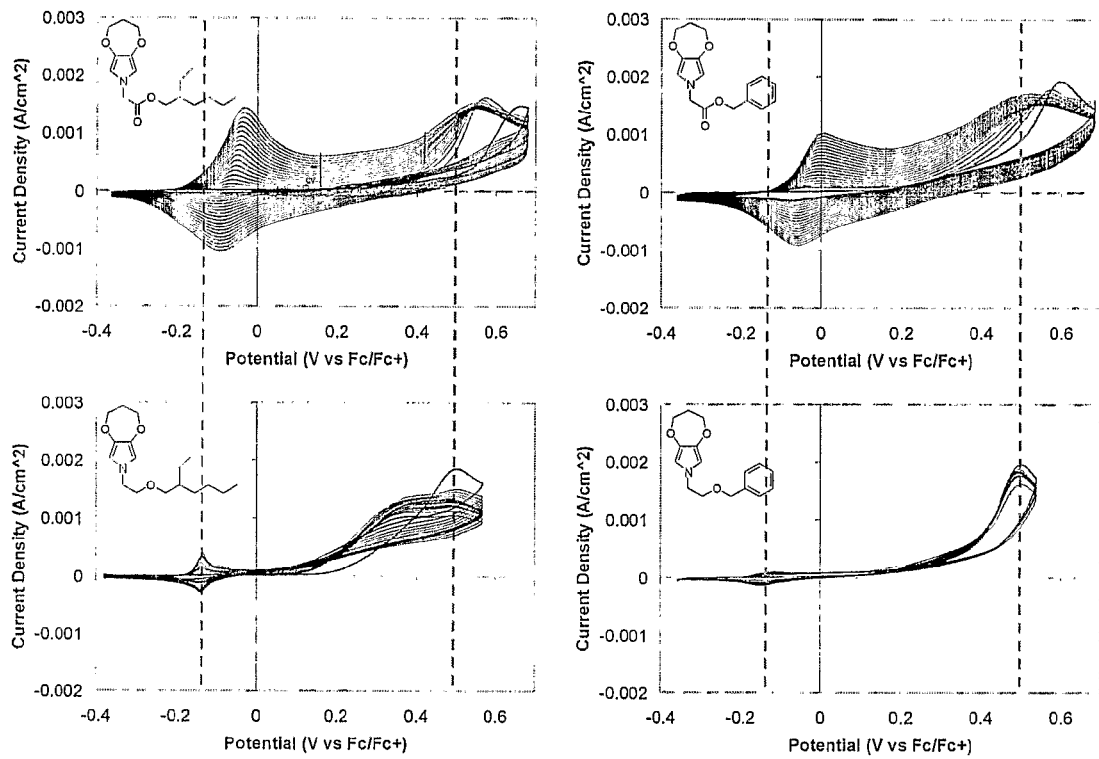
FIG. 10 shows comparative electropolymerizations of benzyl and ethylhexyl esters and ethers substituted (N-acetyl substituted 3,4-propylenedioxypyrrole)s on a Pt button electrode in acetonitrile.

The reduction of the acid to an alcohol permitted the preparation of monomers with ether groups rather than ester groups. FIG. 10 contrasts the electropolymerization of the monomer with a benzyl ester and a ethyl hexyl ester with monomers with benzyl ether and an ethylhexyl ether. The ether derivatives did not polymerize as readily as the ester derivatives ($I_{p,ox}^{20}/I_{p,m}^{0}$=0.07 and 0.22 respectively). The peak monomer oxidation potentials of the ether derivatives exhibit an approximately 100 mV cathodic shift with respect to the ester derivatives (indicated by the vertical lines at positive potential in FIG. 10). Furthermore, the ether derivative polymer $E_{1/2}$ values also show an approximately 100 mV cathodic shift with respect to the ester derivatives (illustrated by the vertical lines at negative potential in FIG. 10). The resulting polymers conceivably allow for better ion flux (better breathability), which is indicated by the incredibly small redox peak separation values ($\Delta E_p$=0.03 V and 0.01 V respectively). Taking into account that the polymer HOMO levels determined by DPV, as described above, are almost exactly equal, this cathodic shift in $E_{1/2}$ may be due to a greater number of ether polymer chains existing in their lowest energy conformational states compared to the esters.

Electrochemical measurements were also conducted on the monomer with the carboxylic acid group and on the monomer with the alcohol group formed upon its reduction. The carboxylic acid exhibited poor solubility in all but the most polar solvents such as water and methanol and exhibited a peak oxidation potential at 0.5 V. This low oxidation potential, was in contrast with that observed for the four ester substituted derivatives. Polymerization of the carboxylic acid was unsuccessful. The monomer with the alcohol group exhibited an incredibly solvent-dependent electropolymerization process. Although the monomer with the alcohol group would not polymerize in acetonitrile and formed a film with unstable electroactivity when polymerized in dichloromethane, galvanostatic polymerization successfully resulted in a very thin polymer film of electrochemically stable polymer from propylene carbonate.

Hence novel N-acetyl ester substituted dihydroxypyrroles which can then be transformed into numerous N-substituted 3,4-alkylenedioxypyrroles which subsequently can be converted into polymers and a method to prepare these compositions of matter have been realized. Although it is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A composition of matter comprising a N-substituted 3,4-alkylenedioxypyrrole of the structure:

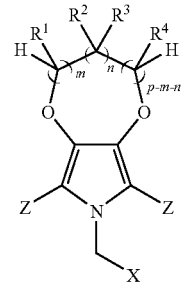

wherein: $R^1$, $R^2$, $R^3$, and $R^4$ are independently hydrogen, methyl, ethyl, $C_3$ through $C_{20}$ straight or branched chain alkyl, aryl, or alkylaryl; p is 2 through 6, m is 1 through p−1, n is 0 through p−2; Z is H or C(O)OH; and X is C(O)$R^5$, wherein $R^5$ is hydrogen, methyl, ethyl, $C_3$ through $C_8$ straight or branched chain alkyl, aryl, O$R^{10}$, or N$R^{11}R^{12}$, wherein $R^{10}$, $R^{11}$, and $R^{12}$, are independently hydrogen, methyl, ethyl, $C_3$ through $C_{20}$ straight or branched chain alkyl, aryl, or alkylaryl.

2. The composition of matter of claim 1, wherein Z is C(O)OH and $R^1$, $R^2$, $R^3$, and $R^4$ are hydrogen.

3. The composition of matter of claim 1, wherein Z is hydrogen and $R^1$, $R^2$, $R^3$, and $R^4$ are hydrogen.

4. The composition of matter of claim 3, wherein X is C(O)$R^5$, $R^5$ is O$R^{10}$, and $R^{10}$ is hydrogen, methyl, ethyl, benzyl, or 2-ethylhexyl.

5. A method for preparing a N-substituted 3,4-alkylenedioxypyrrole comprising the steps of:
providing a nitrogen triester of the structure:

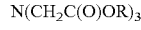

wherein the three R groups are independently methyl, ethyl, $C_3$ through $C_{20}$ straight or branched chain alkyl, or aryl;

condensing said nitrogen triester with dimethyl or diethyloxalate into an ester substituted dihydroxypyrrole of the structure:

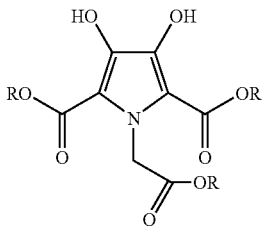

wherein the three R groups are independently methyl, ethyl, $C_3$ through $C_{20}$ straight or branched chain alkyl, or aryl;

annulating said ester substituted dihydroxypyrrole with a difunctionalalkylene of the structure:

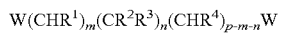

wherein W is Cl, Br, I, sulfate, sulfonate or OH, $R^1$, $R^2$, $R^3$, and $R^4$ are independently hydrogen, methyl, ethyl, $C_3$ through $C_{20}$ straight or branched chain alkyl, aryl, or alkylaryl; p is 2 through 6, m is 1 through p−1, n is 0 through p−2, to form an ester substituted alkylenedioxypyrrole of the structure:

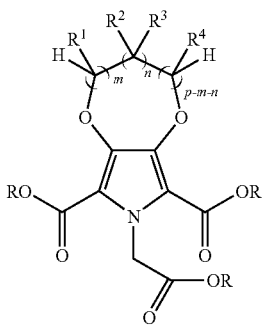

wherein the three R groups are independently methyl, ethyl, $C_3$ through $C_{20}$ straight or branched chain alkyl, or aryl, $R^1$, $R^2$, $R^3$, and $R^4$ are independently hydrogen, methyl, ethyl, $C_3$ through $C_{20}$ straight or branched chain alkyl, aryl, or alkylaryl, and p is 2 through 6, m is 1 through p−1, n is 0 through p−2;

saponifying and neutralizing the annulated ester substituted alkylenedioxypyrrole to form an acid substituted 3,4-alkylenedioxypyrrole of the structure:

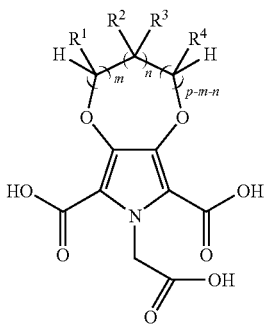

wherein $R^1$, $R^2$, $R^3$, and $R^4$ are independently hydrogen, methyl, ethyl, $C_3$ through $C_{20}$ straight or branched chain alkyl, aryl, or alkylaryl, and p is 2 through 6, m is 1 through p−1, n is 0 through p−2;

decarboxylating of said acid substituted 3,4-alkylenedioxypyrrole to form a 3,4-alkylenedioxypyrrole-acetic acid of the structure:

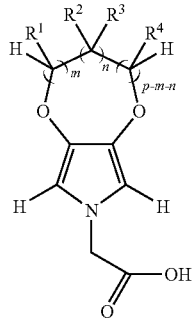

wherein $R^1$, $R^2$, $R^3$, and $R^4$ are independently hydrogen, methyl, ethyl, $C_3$ through $C_{20}$ straight or branched chain alkyl, aryl, or alkylaryl, and p is 2 through 6, m is 1 through p−1, n is 0 through p−2; and transforming of said 3,4-alkylenedioxypyrrole-acetic acid by a single reaction or a series of reactions into said N-substituted 3,4-alkylenedioxypyrrole of the structure:

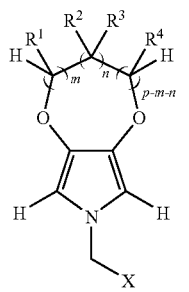

wherein: $R^1$, $R^2$, $R^3$, and $R^4$ are independently hydrogen, methyl, ethyl, $C_3$ through $C_{20}$ straight or branched chain alkyl, aryl, or alkylaryl; p is 2 through 6, m is 1 through p−1, n is 0 through p−2; and X is $C(O)R^5$ wherein $R^5$ is hydrogen, methyl, ethyl, $C_3$ through $C_{20}$ straight or branched chain alkyl, aryl, $OR^{10}$, or $NR^{11}R^{12}$, and wherein $R^{10}$ is independently methyl, ethyl, $C_3$ through $C_{20}$ straight or branched chain alkyl, aryl or alkylaryl, $R^{11}$ and $R^{12}$ are independently hydrogen, methyl, ethyl, $C_3$ through $C_{20}$ straight or branched chain alkyl, aryl or alkylaryl.

6. The method of claim 5, wherein the step of condensing is a Hinsberg condensation.

7. The method of claim 5, wherein the step of annulating is a Williamson etherification and wherein W is Cl, Br, I, sulfate, or sulfonate.

8. The method of claim 5, wherein the step of annulating is a Mitsunobu reaction and wherein W is OH.

9. The method of claim 5, wherein $R^1$, $R^2$, $R^3$, and $R^4$ is hydrogen.

10. The method of claim 5, wherein the step of transforming is deprotonation of said 3,4-alkylenedioxypyrrole-acetic acid with a base and condensation with an alkyl halide, to yield said N-substituted 3,4-alkylenedioxypyrrole wherein X is $C(O)R^5$ and $R^5$ comprises $OR^{10}$ where $R^{10}$ is methyl, ethyl, $C_3$ through $C_{20}$ straight or branched chain alkyl, or alkylaryl.

11. The method of claim 10, wherein said base is $K_2CO_3$ and said alkyl halide is methyl iodide, benzyl bromide, or 1-bromo-2-ethylhexane to yield said N-substituted 3,4-alkylenedioxypyrrole wherein X is $C(O)R^5$ and $R^5$ is $OR^{10}$ where $R^{10}$ is methyl, benzyl, or 2-ethylhexyl.

* * * * *

UNITED STATES PATENT AND TRADEMARK OFFICE
CERTIFICATE OF CORRECTION

| | |
|---|---|
| PATENT NO. | : 7,799,932 B2 |
| APPLICATION NO. | : 11/990042 |
| DATED | : September 21, 2010 |
| INVENTOR(S) | : John R. Reynolds, Ryan M. Walczak and John Sigure Cowart, II |

It is certified that error appears in the above-identified patent and that said Letters Patent is hereby corrected as shown below:

Abstract,
Line 2, "for of formula (I)" should read --of formula (I)--.

Column 1,
Line 43, "throughput" should read --throughout--.

Figure 4:
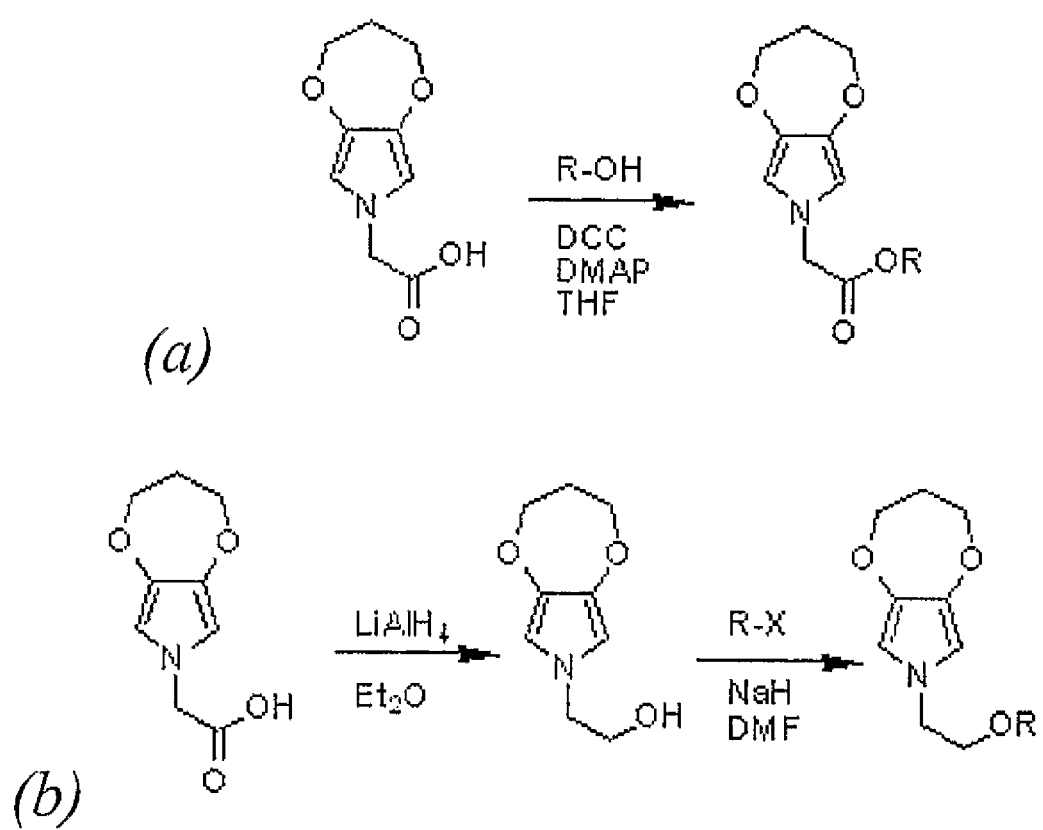
FIG. 4 show the conversion of 3,4-propylenedioxypyrrole-acetic acid to (a) an ester, and (b) to an alcohol and its subsequent conversion to an ether according to embodiments of the invention.

Column 2,
Line 36, "Fig. 4 show" should read --Fig. 4 shows--.

Column 3,
Line 19, "$CR^7= CR^5R^9$," should read --$CR^7= CR^8R^9$,--.

Column 7,
Line 52, "adulated product." should read --annulated product.--.

Column 8,
Line 1, "allyl aryl," should read --alkyl aryl,--.
Line 22, "allylene bridge" should read --alkylene bridge--.
Line 28, "An addition advantage" should read --An additional advantage--.

Column 10,
Line 21, "J=63 Hz)," should read --J=6.3 Hz),--.
Line 25, "55.28; $H^3$," should read --55.28; H,--.
Line 26, "N, 3.80." should read --N, 3.80%.--.
Line 66, "74, 9," should read --74.9,--.

Column 11,
Line 25, "7-(carboxy ethyl)" should read --7-(carboxymethyl)--.
Line 37, "FIRMS (EI):" should read --HRMS (EI):--.

Signed and Sealed this
Third Day of April, 2012

David J. Kappos
*Director of the United States Patent and Trademark Office*

CERTIFICATE OF CORRECTION (continued)
U.S. Pat. No. 7,799,932 B2

Column 13,
Line 29, "TLC $f_f$=0.81" should read --TLC $R_f$=0.81--.

Column 14,
Line 5, "0.1=6.0 Hz," should read --J=6.0 Hz--.
Line 36, "was walked" should read --was warmed--.

Column 19,
Line 7, "($\Delta_{1/2}$" should read --($E_{1/2}$--.

Column 23,
Line 1, Claim 10, "$R^5$ comprises $OR^{10}$" should read --$R^5$ is $OR^{10}$--.